(12) United States Patent
Arcot et al.

(10) Patent No.: US 11,898,204 B2
(45) Date of Patent: Feb. 13, 2024

(54) GENERATION OF SINGLE-STRANDED CIRCULAR DNA TEMPLATES FOR SINGLE MOLECULE SEQUENCING

(71) Applicants: Roche Sequencing Solutions, Inc., Pleasanton, CA (US); Kapa Biosystems, Inc., Wilmington, MA (US)

(72) Inventors: Aruna Arcot, Fremont, CA (US); Daleen Badenhorst, Wellington (ZA); Rui Chen, Fremont, CA (US); Toummy Guettouche, Pleasanton, CA (US); Ashley Hayes, San Francisco, CA (US); Jenny A. Johnson, Castro Valley, CA (US); Severine Margeridon, Castro Valley, CA (US); Martin Ranik, Cape Town (ZA); Persis Wadia, Fremont, CA (US); Alexandra Hui Wang, Mountain View, CA (US)

(73) Assignees: Roche Sequencing Solutions, Inc., Pleasanton, CA (US); KAPA Biosystems, Inc., Wilmington, MA (US)

( * ) Notice: Subject to any disclaimer, the term of this patent is extended or adjusted under 35 U.S.C. 154(b) by 834 days.

(21) Appl. No.: 16/977,421

(22) PCT Filed: Feb. 28, 2019

(86) PCT No.: PCT/EP2019/054938
§ 371 (c)(1),
(2) Date: Sep. 1, 2020

(87) PCT Pub. No.: WO2019/166530
PCT Pub. Date: Sep. 6, 2019

(65) Prior Publication Data
US 2023/0183797 A1 Jun. 15, 2023

Related U.S. Application Data

(60) Provisional application No. 62/685,817, filed on Jun. 15, 2018, provisional application No. 62/638,034, filed on Mar. 2, 2018.

(51) Int. Cl.
 C12Q 1/6869 (2018.01)
 C12Q 1/6874 (2018.01)
 C12N 15/10 (2006.01)
 C12Q 1/6855 (2018.01)

(52) U.S. Cl.
 CPC ....... *C12Q 1/6874* (2013.01); *C12N 15/1068* (2013.01); *C12Q 1/6855* (2013.01)

(58) Field of Classification Search
 None
 See application file for complete search history.

(56) References Cited

U.S. PATENT DOCUMENTS

| 5,874,260 A | 2/1999 | Cleuziat et al. |
| 9,487,807 B2 | 11/2016 | Eshoo et al. |
| 9,938,570 B2 | 4/2018 | Spier |
| 2018/0208966 A1 | 7/2018 | Ilik |

FOREIGN PATENT DOCUMENTS

| WO | 2010148039 A2 | 12/2010 |
| WO | 2012/012037 A1 | 1/2012 |
| WO | 2017/162754 A1 | 9/2017 |
| WO | 2017162754 A1 | 9/2017 |
| WO | 2018/015365 A1 | 1/2018 |
| WO | 2018015365 A1 | 1/2018 |
| WO | 2019/166565 A1 | 9/2019 |

OTHER PUBLICATIONS

International Searching Authority, "International Preliminary Report on Patentability" for International Patent Application No. PCT/EP2019/054938 (dated Sep. 8, 2020).
International Searching Authority, "International Search Report" for International Patent Application No. PCT/EP2019/054938 (dated Sep. 6, 2019).
International Searching Authority, "Written Opinion of the International Searching Authority" for International Patent Application No. PCT/EP2019/054938 (dated Sep. 6, 2019).
Cheulhee Jung, "A primerless molecular diagnostic: phosphorothioated-terminal hairpin formation and self-priming extension (PS-THSP)", Article, Mar. 31, 2016, 1-9, N/A.

*Primary Examiner* — Christopher M Gross
(74) *Attorney, Agent, or Firm* — Eric Grant Lee (57) ABSTRACT

The invention is a novel method of separately sequencing each strand of a nucleic acid involving the use of an adaptor comprising a strand cleavage site or a strand synthesis termination site. The adaptor may also be self-priming at the strand cleavage site.

15 Claims, 7 Drawing Sheets
Specification includes a Sequence Listing.

GENERATION OF SINGLE-STRANDED CIRCULAR DNA TEMPLATES FOR SINGLE MOLECULE SEQUENCING

CROSS-REFERENCE TO RELATED APPLICATIONS

This application is a national stage of the International Application Ser. No. PCT/EP2019054938 filed on Feb. 28, 2019, which claims priority to the U.S. Provisional Application Ser. No. 62/638,034 filed on Mar. 2, 2018, both of which are incorporated herein by reference for all purposes.

SEQUENCE LISTING

The instant application contains a Sequence Listing which has been submitted electronically in ASCII format and is hereby incorporated by reference in its entirety. Said ASCII copy, created on Dec. 18, 2020, is named P34639-US-1_SL.txt and is 2,382 bytes in size.

FIELD OF THE INVENTION

The invention relates to the field of nucleic acid analysis and more specifically, to preparing templates for nucleic acid sequencing.

BACKGROUND OF THE INVENTION

Single molecule nucleic acid sequencing includes a step of preparing library of target molecules for the sequencing step. Linear nucleic acid libraries of the coexist with linear nucleic acid byproducts that impede performance of the sequencing method. There are library preparation methods that produce circular double stranded templates that allow both strands of the target sequence to be read multiple times in a contiguous polymerase read. See U.S. Pat. Nos. 7,302,146 and 8,153,375. Some applications require reading long target molecules making a separate single-pass read or each strand more desirable. The present invention is a method of efficiently generating libraries and sequencing each strand of the target nucleic acid separately. The method has multiple advantages described in detail below.

SUMMARY OF THE INVENTION

In some embodiments, the invention is a method of separately sequencing each strand of a target nucleic acid comprising the steps of: in a reaction mixture, joining the ends of a double stranded target nucleic acid to adaptors to form a doubly-adapted target nucleic acid wherein the adaptor is a single strand forming a double stranded stem and a single-stranded loop and the stem comprises at least one strand cleavage site; contacting the reaction mixture with an exonuclease thereby enriching for the doubly-adapted target nucleic acid; contacting the reaction mixture with a cleavage agent to cleave the doubly-adapted target nucleic acid at the cleavage sites forming extendable termini on each strand; extending the extendable termini thereby separately sequencing each strand of the target nucleic acid, wherein extension is terminated at the cleavage site and does not proceed onto the complementary strand. The joining could be by ligation, e.g., of cohesive ends of the target nucleic acid and the adaptor. The exonuclease may be selected from one or both of Exonuclease III and Exonuclease VII. The adaptor may comprise at least one barcode. In some embodiments, the cleavage site comprises one or more deoxyuracils and the cleavage agent comprises Uracil-DNA-N-glycosylase (UNG) and an endonuclease, e.g., Endonuclease III, Endonuclease IV, or Endonuclease VIII. In some embodiments, the cleavage site comprises one or more ribonucleotides and the cleavage agent comprises RNaseH. In some embodiments, the cleavage site comprises one or more abasic sites and the cleavage agent comprises an endonuclease selected from Endonuclease III, Endonuclease IV, and Endonuclease VIII. The adaptor may comprise an exonuclease protection nucleotide such as one containing a phosphorothioate group.

In some embodiments, the adaptor comprises a ligand for a capture moiety. For example, the ligand could be biotin or modified biotin and the capture moiety comprises avidin or streptavidin. The ligand could be an adenosine sequence (oligo-dA) and the capture moiety comprises a thymidine sequence (oligo-dT).

In some embodiments, the method further comprises a target enrichment step prior to sequencing, e.g., with target-specific probes.

In some embodiments, the invention is a method of making a library of a target nucleic acids for separately sequencing each strand of a target nucleic acid, the method comprising the steps of: in a reaction mixture, joining the ends of double stranded target nucleic acids to adaptors to form a doubly-adapted target nucleic acids wherein the adaptor is a single strand forming a double stranded stem and a single stranded loop and the stem comprises a strand cleavage site, contacting the reaction mixture with an exonuclease thereby enriching for the doubly-adapted target nucleic acids; contacting the reaction mixture with a cleavage agent to cleave the doubly-adapted target nucleic acids at the cleavage sites forming extendable termini on each strand. In some embodiments, the invention is a method of determining the sequence of a library of target nucleic acid in a sample, the method comprising the steps of: forming a library of target nucleic acids as set forth above; extending the extendable termini thereby separately sequencing each strand of the target nucleic acids in the library, wherein the extension is terminated at the cleavage site and does not proceed onto the complementary strand.

In some embodiments, the invention is a method of separately sequencing each strand of a target nucleic acid comprising the steps of: in a reaction mixture, joining the ends of a double stranded target nucleic acid to adaptors to form a doubly-adapted target nucleic acid wherein the adaptor is a single strand forming a double stranded stem and a single-stranded loop, and the loop comprises a primer binding site and the adaptor further comprises strand synthesis termination site and; contacting the reaction mixture with an exonuclease thereby enriching for the doubly-adapted target nucleic acid; contacting the reaction mixture with a primer capable of hybridizing to the primer binding sites; extending the primers thereby separately sequencing each strand of the target nucleic acid, wherein extension is terminated at the strand synthesis termination site and does not proceed onto the complementary strand. The strand synthesis termination site can be selected from a nick, a gap, an abasic nucleotide and a non-nucleotide linker.

In some embodiments, the invention is a method of making a library for separately sequencing each strand of a target nucleic acid comprising the steps of: in a reaction mixture, joining the ends of double stranded target nucleic acids to adaptors to form doubly-adapted target nucleic acids wherein the adaptor is a single strand forming a double stranded stem and a single-stranded loop, and the loop comprises a primer binding site and the adaptor further comprises strand synthesis termination site; contacting the reaction mixture with an exonuclease thereby enriching for the doubly-adapted target nucleic acids and forming a library of doubly-adapted target nucleic acids. In some embodiments, the invention is a method of determining the sequence of a library of target nucleic acid in a sample, the method comprising the steps of: forming a library of target nucleic acids by the method set forth above; contacting the library with a primer capable of hybridizing to the primer binding sites; extending the primers thereby separately sequencing each strand of the target nucleic acids in the library, wherein extension is terminated at the strand synthesis termination site and does not proceed onto the complementary strand.

DETAILED DESCRIPTION OF THE INVENTION

Definitions

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

The term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. Some examples of non natural bases include those described in, e.g., Seela et al., (1999) *Helv. Chim. Acta* 82:1640. The non-natural bases may have a particular function, e.g., increasing the stability of the nucleic acid duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. Oligonucleotides are prepared by any suitable method known in the art, for example, by a method involving direct chemical synthesis as described in Narang et al. (1979) *Meth. Enzymol.* 68:90.99; Brown et al. (1979) *Meth. Enzymol.* 68:109.151; Beaucage et al. (1981) *Tetrahedron Lett.* 22:1859-1862; Matteucci et al. (1981) *J. Am. Chem. Soc.* 103:3185.3191.

The term "modified nucleotide" is used herein to describe a nucleotide in DNA with a base other than the four conventional DNA bases consisting of adenosine, guanosine, thymidine and cytosine, dA, dG, dC and dT are conventional nucleotides. However, deoxyuracil (dU) and deoxyinosine (dI) are modified nucleotides in DNA. Ribonucleotides (rA, rC, rU and rG) inserted into DNA are also considered "modified nucleotides" in the context of the present invention. Finally, non-nucleotide moieties (such as PEG) Inserted in place of nucleotides into a nucleic acid strand are also considered "modified nucleotides" in the context of the present invention.

The term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion. The term "adapted target nucleic acid" refers to a nucleic acid to which an adaptor is conjugated at one or both ends.

The term "ligation" refers to a condensation reaction joining two nucleic acid strands wherein a 5' phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified. Barcodes can be incorporated into various nucleic acids. Barcodes are sufficiently long e.g., 2, 5, 20 nucleotides, so that in a sample, the nucleic acids incorporating the barcodes can be distinguished or grouped according to the barcodes.

The term "multiplex identifier" or "MID" refers to a barcode that identifies a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The term "unique molecular identifier" or "UID" refers to a barcode that identifies a nucleic acid to which it is attached. All or substantially all the target nucleic acids from the same sample will have different UIDs. All or substantially all of the progeny (e.g., amplicons) derived from the same original target nucleic acid will share the same UID.

The terms "universal primer" and "universal priming binding site" or "universal priming site" refer to a primer and primer binding site present in (typically, through in vitro addition to) different target nucleic acids. The universal priming site is added to the plurality of target nucleic acids using adaptors or using target-specific (non-universal) primers having the universal priming site in the 5'-portion. The universal primer can bind to and direct primer extension from the universal priming site.

More generally, the term "universal" refers to a nucleic acid molecule (e.g., primer or other oligonucleotide) that can be added to any target nucleic acid and perform its function irrespectively of the target nucleic acid sequence. The universal molecule may perform its function by hybridizing to the complement, e.g., a universal primer to a universal primer binding site or a universal circularization oligonucleotide to a universal primer sequence.

As used herein, the terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "amplification" refers to a process of making additional copies of the target nucleic acid. Amplification can have more than one cycle, e.g., multiple cycles of exponential amplification. Amplification may have only one cycle (making a single copy of the target nucleic acid). The copy may have additional sequences, e.g., those present in the primers used for amplification. Amplification may also produce copies of only one strand (linear amplification) or preferentially one strand (asymmetric PCR).

The term "sequencing" refers to any method of determining the sequence of nucleotides in the target nucleic acid.

The term "self-priming adaptor" refers to an adaptor capable of initiating strand extension (copying of the strand) from the adaptor itself. The self-priming adaptor is contrasted with a traditional adaptor comprising a primer binding site where a separate primer molecule binds to the adaptor to initiate strand extension from the primer.

Single molecule sequencing methods involve a step of generating a library of adapted target nucleic acids. In some methods, the library is made of linear adapted target nucleic acids. During a linear library preparation workflow, sequencing adapters (Y or h adapter) are ligated to double-stranded DNA prior to loading onto the sequencer. Unfortunately, the ligation step is not 100% efficient and partially-ligated products or un ligated products are generated. Those byproducts reduce active sequencing yield and performance of the instrument for example, by competing for binding to the sequencing polymerase. To enrich for fully ligated products, modified adapters have been designed. The new adaptors allow for an exonuclease step that removes partially and un-ligated products.

The method of the invention has numerous advantages. The method enables long single-molecule sequencing of highly enriched libraries (by virtue of the exonuclease-mediated enrichment.) Furthermore, the use of self-priming adaptors streamlines the sequencing workflow by obviating the need for another primer and primer annealing step. Yet further, there is no strand orientation bias because identical adaptors are ligated to both ends of each target nucleic acid and identical priming mechanism is used. Yet further, different types of target nucleic acids are compatible with these adapters, e.g., genomic DNA (gDNA) or amplification products. The size of the target nucleic acid and the final read lengths are only limited by the sequencing platform utilized and not limited by the library design.

The present invention comprises detecting a target nucleic acid in a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or fecal samples). The sample may comprise whole blood or blood fractions where tumor cells may be present. In some embodiments, the sample, especially a liquid sample may comprise cell free material such as cell free DNA or RNA including cell-free tumor DNA or tumor RNA. The present invention is especially suitable for analyzing rare and low quantity targets. In some embodiments, the sample is a cell-free sample, e.g., cell-free blood-derived sample where cell-free tumor DNA or tumor RNA are present. In other embodiments, the sample is a cultured sample, e.g., a culture or culture supernatant containing or suspected to contain an infectious agent or nucleic acids derived from the infectious agent. In some embodiments, the infectious agent is a bacterium, a protozoan, a virus or a mycoplasma.

A target nucleic acid is the nucleic acid of interest that may be present in the sample. In some embodiments, the target nucleic acid is a gene or a gene fragment. In other embodiments, the target nucleic acid contains a genetic variant, e.g., a polymorphism, including a single nucleotide polymorphism or variant (SNP or SNV), or a genetic rearrangement resulting e.g., in a gene fusion. In some embodiments, the target nucleic acid comprises a biomarker. In other embodiments, the target nucleic acid is characteristic of a particular organism, e.g., aids in identification of the pathogenic organism or a characteristic of the pathogenic organism, e.g., drug sensitivity or drug resistance. In yet other embodiments, the target nucleic acid is characteristic of a human subject, e.g., the HLA or KIR sequence defining the subject's unique HLA or KIR genotype. In yet other embodiments, all the sequences in the sample are target nucleic acids e.g., in shotgun genomic sequencing.

In an embodiment of the invention, a double-stranded target nucleic acid is converted into the template configuration of the invention. In some embodiments, the target nucleic acid occurs in nature in a single-stranded form (e.g., RNA, including mRNA, microRNA, viral RNA; or single-stranded viral DNA). The single-stranded target nucleic acid is converted into double-stranded form to enable the further steps of the claimed method.

Longer target nucleic acids may be fragmented although in some applications longer target nucleic acids may be desired to achieve a longer read. In some embodiments, the target nucleic acid is naturally fragmented, e.g., circulating cell-tree DNA (ctDNA) or chemically degraded DNA such as the one founds in preserved samples. In other embodiments, the target nucleic acid is fragmented in vitro, e.g., by physical means such as sonication or by endonuclease digestion, e.g., restriction digestion.

In some embodiments, the invention comprises a target enrichment step. The enrichment may be by capturing the target sequences via one or more targets-specific probes. The nucleic acids in the sample may be denatured and contacted with single stranded target-specific probes. The probes may comprise a ligand for an affinity capture moiety so that after hybridization complexes are formed, they are captured by providing the affinity capture moiety. In some embodiments, the affinity capture moiety is avidin or streptavidin and the ligand is biotin or desthiobiotin. In some embodiments, the moiety is bound to solid support. As described in further detail below, the solid support may comprise superparamagnetic spherical polymer particles such as DYNABEADS™ magnetic beads or magnetic glass particles.

In some embodiments of the present invention, adaptor molecules are ligated to the target nucleic acid. The ligation can be a blunt-end ligation or a more efficient cohesive-end ligation. The target nucleic acid or the adaptors may be rendered blunt-ended by "end repair" comprising strand-filling, i.e., extending a 3'-terminus by a DNA polymerase to eliminate a 5'-overhang. In some embodiments, the blunt-ended adaptors and target nucleic acid may be rendered cohesive by addition of a single nucleotide to the 3'-end of the adaptor and a single complementary nucleotide to the 3'-ends of the target nucleic acid, e.g., by a DNA polymerase or a terminal transferase. In yet other embodiments, the adaptors and the target nucleic acid may acquire cohesive ends (overhangs) by digestion with restriction endonucleases. The latter option is more advantageous for known target sequences that are known to contain the restriction enzyme recognition site. In some embodiments, other enzymatic steps may be required to accomplish the ligation. In some embodiments, a polynucleotide kinase may be used to add 5'-phosphates to the target nucleic acid molecules and adaptor molecules.

Figure 3:
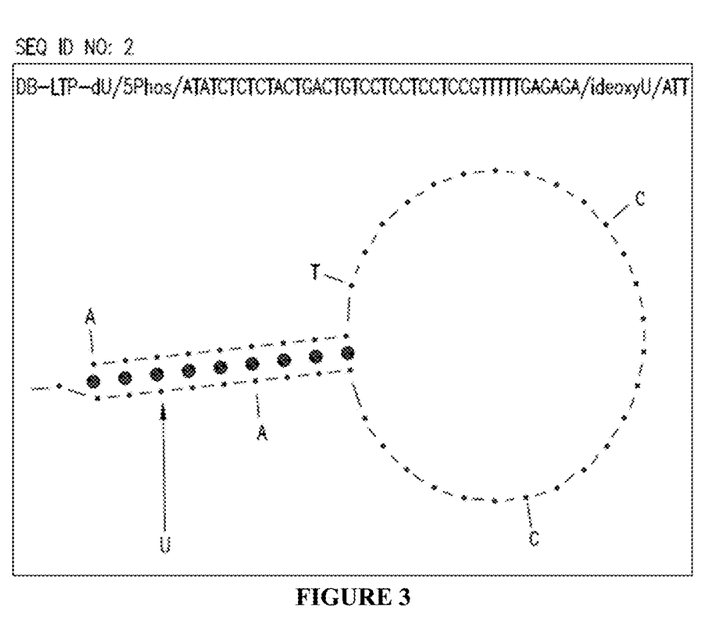
FIG. 3 illustrates the stem-loop adaptor structure.
Figure 4:
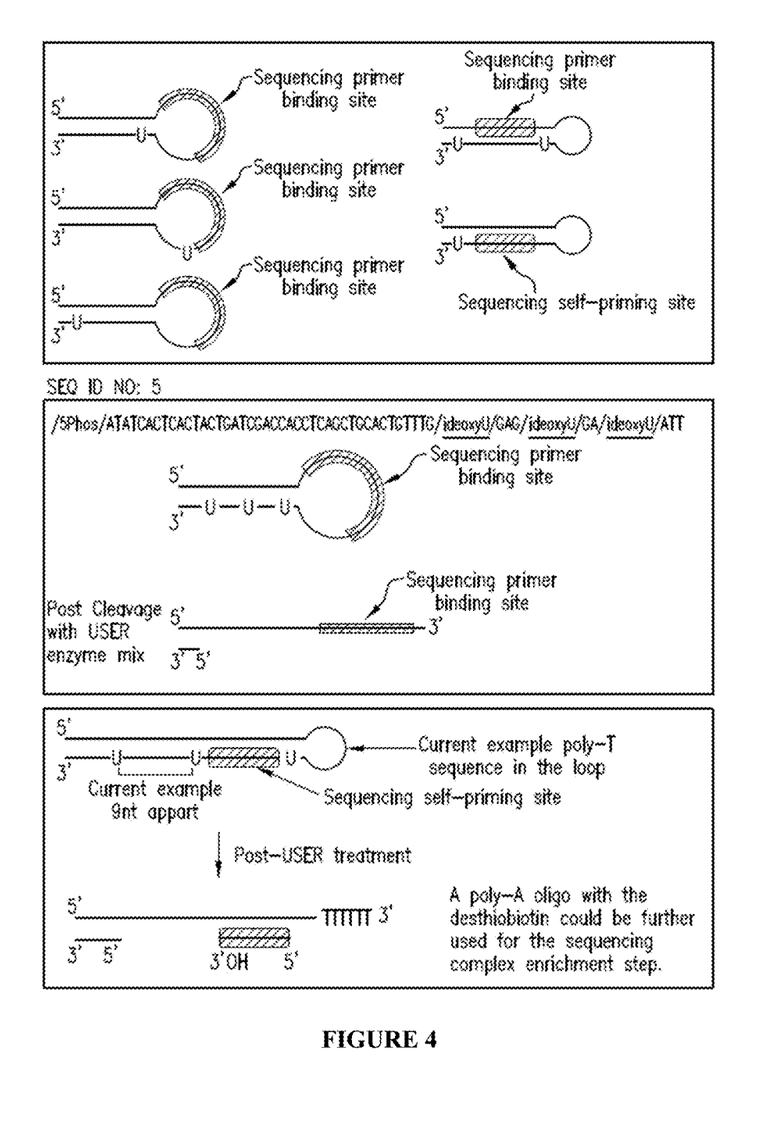
FIG. 4 illustrates different placement of the cleavage site in the adaptor shown in FIG. 3.
Figure 7:
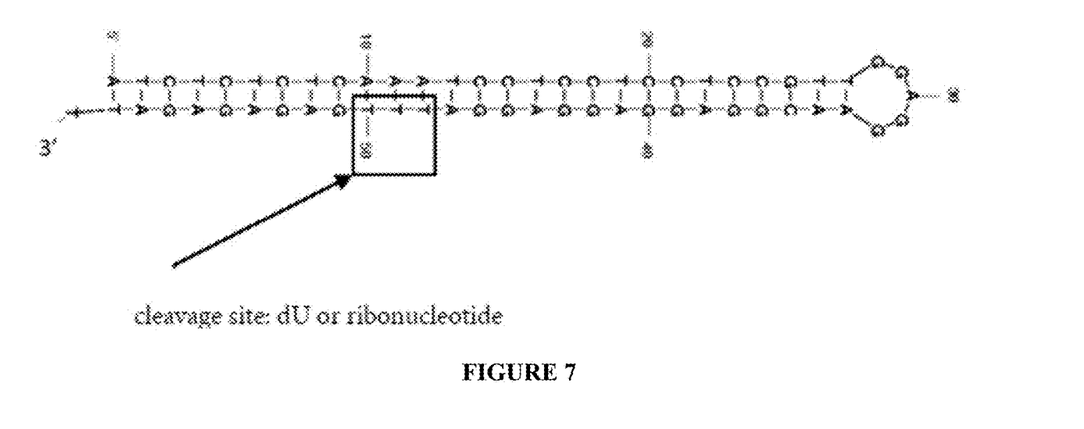
FIG. 7 is a diagram of a self-priming hairpin adaptor.

In some embodiments, adaptors comprise a double stranded portion (stem) and a single stranded portion (loop) distal to the stem. The stem comprises a strand cleavage site (FIG. 3). In some embodiments, the loop comprises a primer binding site (FIG. 4). In such embodiments, the annealed primer can initiate copying of the strand. In some embodiments, adaptors comprise a double stranded portion (stem) and a single stranded portion (loop), including a very small loop distal to the stem. Such adaptors may be stem-loop or hairpin adaptors (FIG. 7). The stem comprises a strand cleavage site enabling the cleaved adaptor to self-prime, i.e., initiate copying of the strand without a separate primer.

In some embodiments, the adaptor molecules are in vitro synthesized artificial sequences. In other embodiments, the adaptor molecules are in vitro synthesized naturally-occurring sequences. In yet other embodiments, the adaptor molecules are isolated naturally occurring molecules.

In some embodiments, the invention comprises introduction of barcodes into the target nucleic acids by ligation of barcode-containing adaptors. Sequencing individual molecules typically requires molecular barcodes such as described e.g., in U.S. Pat. Nos. 7,393,665, 8,168,385, 8,481,292, 8,685,678, and 8,722,368. A unique molecular barcode is a short artificial sequence added to each molecule in a sample such as a patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy. See U.S. patent application Ser. Nos. 14/209,807 and 14/774,518. Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample. See Id.

In some embodiments of the present invention, adaptors comprise one or more barcodes. A barcode can be a multiplex sample ID (MID) used to identify the source of the sample where samples are mixed (multiplexed). The barcode may also serve as a UID used to identify each original molecule and its progeny. The barcode may also be a combination of a UID and an MID. In some embodiments, a single barcode is used as both UID and MID.

In some embodiments, each barcode comprises a predefined sequence. In other embodiments, the barcode comprises a random sequence. Barcodes can be 1-40 nucleotides long.

In the method of the invention, the adaptor comprises a strand cleavage site. The cleavage site is selected from a modified nucleotide for which a specific endonuclease is available. A non-limiting list of examples of modified nucleotide-endonuclease pairs includes deoxyuracil—Uracil-N-DNA glycosylase (UNG) plus endonuclease; abasic site—AP nuclease; 8-oxoguanine-8-oxoguanine DNA glycosylase (also known as Fpg (formamidopyrimidine [fapy]-DNA glycosylase)); deoxyinosine—alkyladenine glycosylase (AAG) plus endonuclease and ribonucleotide—RNaseH.

In some embodiments of the invention, the cleavage site is used to generate an extendable 3'-end. In such embodiments, the cleavage site is located in the stem portion of the adaptor so that copying of the complementary strand could be initiated.

Different cleavage agents generate different products. In some embodiments, endonuclease VIII (Endo VIII) is used which creates a mixture of products, including 3' P. In other embodiments, endonuclease III (Endo III) is used which creates a 3'-phospho-α,β-unsaturated aldehyde. In yet other embodiments, endonuclease IV (Endo IV) is used which creates a 3'-OH end. The non-extendable ends are advantageous in embodiments where a separate sequencing primer is used. An extendable 3'-end (3'-OH) is advantageous where there is no separate sequencing primer and the sequencing reaction is self-primed by the extendable 3'-end.

In other embodiments, the cleavage site is used as a strand synthesis (extension) terminator. In such embodiments, the cleavage site is located anywhere in the adaptor that is upstream of the primer binding site.

In some embodiments, the method includes a step of contacting the reaction mixture with an endonuclease capable of cleaving the cleavage site under the conditions where such cleavage could occur.

In some embodiments, the sequencing reaction comprises a self-priming step. Endonuclease strand cleavage at the cleavage site generates a free 3'-end that can be extended in a sequencing by synthesis reaction without a separate sequencing primer (FIG. 7).

In some embodiments, the cleavage site acts as a strand termination step. Having extended the strand (or a primer) from one of the two adaptors in the adapted target nucleic acid, the sequencing DNA polymerase reaches the cleavage site in the second adaptor in the target nucleic acid. The strand break will act as a strand extension terminator. In other embodiments, the modified nucleotide is a non-nucleotide polymer such as polyethylene glycol (PEG), e.g., hexaethylene glycol (HEG). These moieties are not cleaved by endonucleases but act as strand synthesis terminators in the nucleic acid strand that is being copied.

In some embodiments, the method includes affinity capture of the adapted target nucleic acids or any other sequencing intermediate (e.g., ternary complex of the pore protein, DNA polymerase and the template used in nanopore sequencing). To that end, the adaptors may incorporate an affinity ligand (e.g., biotin) that will enable the target to be captured by an affinity capture moiety (e.g., via streptavidin). In some embodiments, desthiobiotin is used. In some embodiments, the affinity capture utilizes the affinity molecule (e.g., streptavidin) bound to solid support. The solid support may be capable of suspension in a solution (e.g., a glass bead, a magnetic bead, a polymer bead or another like particle), or a solid-phase support (e.g., a silicon wafer, a glass slide, or the like). Examples of solution-phase supports include superparamagnetic spherical polymer particles such as DYNABEADS' magnetic beads or magnetic glass particles such as described in U.S. Pat. Nos. 656,568, 6,274,386, 7,371,830, 6,870,047, 6,255,477, 6,746,874 and 6,258,531. In some embodiments, the affinity ligand is a nucleic acid sequence and its affinity molecule is a complementary sequence. In some embodiments, the solid substrate comprises a poly-T oligonucleotide while the adaptor comprises at least partially single-stranded poly-A portion.

In some embodiments, strand separation is enhanced by various agents selected from the single-strand binding protein, e.g., bacterial SSB, low complexity DNA $C_o t$ DNA (DNA enriched for repetitive sequences), or chemical agents such as alkali, glycerol, urea, DMSO or formamide.

In some embodiments, the invention comprises an exonuclease digestion step after the adaptor ligation step. The exonuclease will eliminate any nucleic acids comprising free termini from the reaction mixture. The exonuclease digestion will enrich for doubly-adapted target nucleic acids that are topologically circular, i.e., do not contain free termini. Unligated target nucleic acids, nucleic acids ligated to only one adaptor and excess adaptors will be eliminated from the reaction mixture.

The exonuclease may be a single strand-specific exonuclease, a double strand-specific exonuclease or a combination thereof. The exonuclease may be one or more of Exonuclease I, Exonuclease III and Exonuclease VII.

In some embodiments, the invention includes a method of making a library of sequencing ready adapted target nucleic acids as described herein as well as the library produced by the method. Specifically, the library comprises a collection of adapted target nucleic acids derived from nucleic acids present in a sample. The adapted target nucleic acid molecules of the library are topologically circular molecules comprising target sequences joined with adaptor sequences at each end and comprising a cleavage site and optionally, a primer binding site.

In some embodiments, the present invention comprises detecting target nucleic acids in a sample by nucleic acid sequencing. Multiple nucleic acids, including all the nucleic acids in a sample may be converted into the library of the invention and sequenced.

In some embodiments, the method further comprises a step of eliminating damaged or degraded targets from the library in order to improve the quality and length of sequencing reads. The step may comprise contacting the library with one or more of uracil DNA N-glycosylase (UNG or UDG), AP nuclease and Fpg (formamidopyrimidine [fapy]-DNA glycosylase), also known as 8-oxoguanine DNA glycosylase in order to degrade such damaged target nucleic acids.

Sequencing can be performed by any method known in the art. Especially advantageous is the high throughput single molecule sequencing capable of reading long target nucleic acids. Examples of such technologies include the Pacific Biosciences platform utilizing the SMRT (Pacific Biosciences, Menlo Park. Cal.) or a platform utilizing nanopore technology such as those manufactured by Oxford Nanopore Technologies (Oxford, UK) or Roche Sequencing Solutions (Roche Genia, Santa Clara, Cal.) and any other presently existing or future DNA sequencing technology that does or does not involve sequencing by synthesis. The sequencing step may utilize platform specific sequencing primers.

Analysis and Error Correction

In some embodiments, the sequencing step involves sequence analysis including a step of sequence aligning. In some embodiments, aligning is used to determine a consensus sequence from a plurality of sequences, e.g., a plurality having the same barcodes (UID). In some embodiments barcodes (UIDs) are used to determine a consensus from a plurality of sequences all having an identical barcode (UID). In other embodiments, barcodes (UIDs) are used to eliminate artifacts, i.e., variations existing in some but not all sequences having an identical barcode (UID). Such artifacts resulting from sample preparation or sequencing errors can be eliminated.

In some embodiments, the number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

Figure 1:
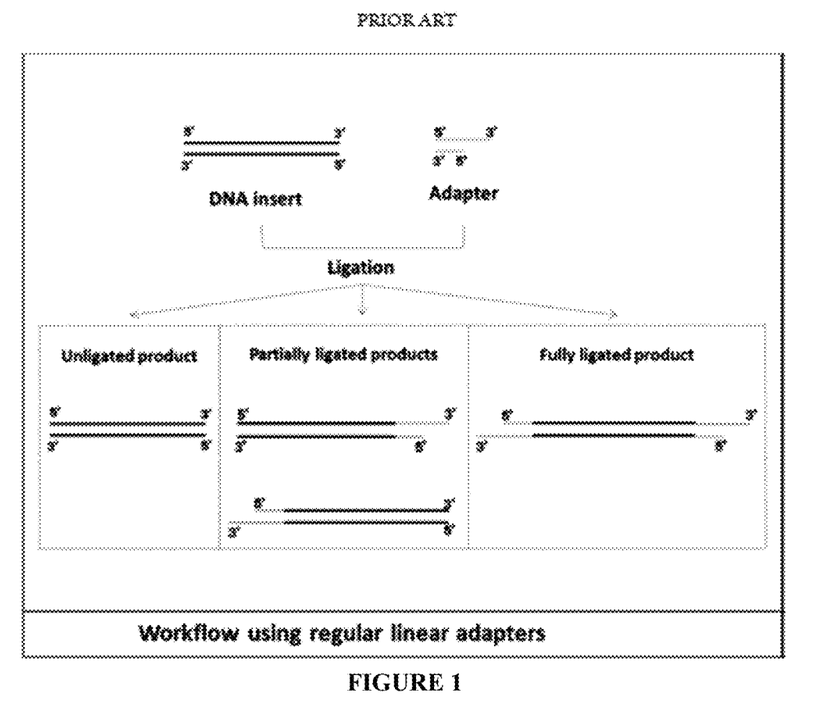
FIG. 1 is a diagram of the existing method of forming adapted nucleic acids.
Figure 5:
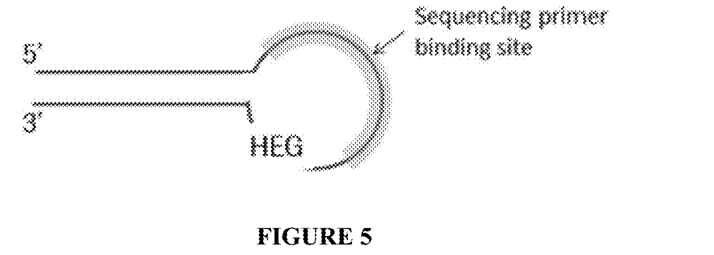
FIG. 5 illustrates an adaptor with a non-nucleotide (HEG) cleavage site.

The prior art method of forming a library of adapted target nucleic acids e.g., for amplification and sequencing is shown on FIG. 1. The library comprises linear adapted target nucleic acids. In contrast the method of the invention (shown in FIG. 2), forms topologically closed nucleic acids that are resistant to exonuclease digestion and can be enriched using exonucleases. One embodiment of the adaptor having one deoxyuracils (dU) is shown on FIG. 3. Other embodiments of adaptors with multiple dUs are illustrated in FIG. 4 and FIG. 7. Yet another embodiment of the adaptor has a non-nucleotide polymer such as polyethylene glycol (PEG), e.g., hexaethylene glycol (HEG) instead of a dU (FIG. 5).

Figure 2:
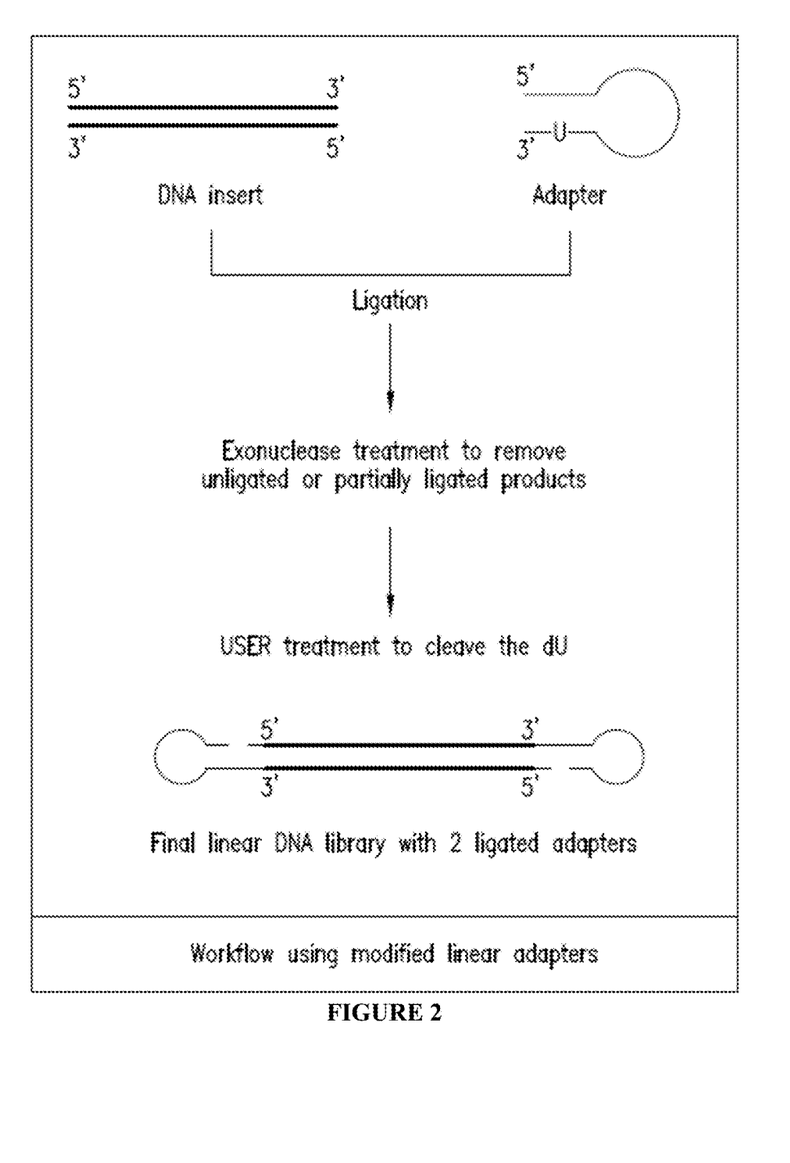
FIG. 2 is a workflow of the invention where the adaptors have a secondary structure and contain a cleavage site.

The method starts with ligating a stem-loop adaptor to the ends of double-stranded nucleic acid in a reaction mixture (FIG. 2). The resulting structure is a topologically circular (closed) nucleic acid lacking free 5' and 3' termini. Any unligated target nucleic acids and unused adaptor molecules may be removed from the reaction mixture thus enriching for adapted target nucleic acids (FIG. 2). The adaptor comprises at least one deoxyuracil (dU) in the stem portion which is to become a strand cleavage site (FIG. 3). Next, a uracil-DNA glycosylase (e.g., UNG) is used to cleave the uracil exposing an abasic site in the DNA. Further, a strand break is made using an AP lyase, endonuclease (e.g., Endonuclease IV) or non-enzymatic reagents or conditions to generate a single-strand break (nick).

Next, the reaction mixture is contacted with a sequencing primer that binds to primer binding site in the single stranded portion of the adaptor and is capable of initiating a sequencing primer extension reaction. The primer binding site in the single stranded portion may be in the loop portion (FIG. 4). The primer binding site in the single stranded portion may also be in the region opposite to the gap exposed after endonuclease cleavage (FIG. 4). The primer extension proceeds up to and terminates at the cleavage site (nick) in the opposite-side adaptor in the adapted target nucleic acid.

In another embodiment, adaptor shown in FIG. 7 is used. This embodiment of the method also starts with ligating a stem-loop adaptor to the ends of double-stranded nucleic acid in a reaction mixture. In this embodiment, a separate sequencing primer is not needed and the loop region of the adaptor need not contain the sequencing primer binding site for the sequencing step. The adaptor comprises one or more deoxyuracils (dU) in the stem portion which are to become a strand cleavage site. The resulting adapted target nucleic acid is a topologically circular (closed) nucleic acid lacking free 5' and 3' termini. Any unligated target nucleic acids and unused adaptor molecules may be removed from the reaction mixture thus enriching for adapted target nucleic acids. For example, treatment with an exonuclease targeting free 5'- or 3'-ends may be used.

Next, a uracil-DNA glycosylase (e.g., UNG) is used to cleave the one or more uracils exposing abasic sites in the DNA. Further, a strand break is made using an AP lyase, endonuclease (e.g., Endonuclease IV or Exonuclease VIII) or non-enzymatic reagents or conditions to generate a single-strand break (nick). If more than one deoxyuracil is present, a gap is generated. Next, the free 3'-end of the strand in the nick (or gap) is extended in a sequencing strand extension reaction. In some embodiments, the adaptor comprises nucleotides resistant to exonuclease cleavage. These nucleotides (e.g., phosphorothioate nucleotides) are positions near the cleavage site to protect the extendable 3' end from exonuclease degradation. The extension proceeds up to and terminates at the cleavage site (nick or gap) in the opposite-side adaptor in the adapted target nucleic acid.

EXAMPLES

Example 1. Forming and Sequencing a Library with a dU Containing Stem-Loop Adaptor In this example, a stem-loop adaptor diagrammed in FIG. 3 was used. Adaptors for SMRT-based sequencing system (SEQ ID Nos: 3 and 4) and for a nanopore-based system (SEQ ID Nos: 1 and 2) were made. Each adapter was made with and without a deoxyuracils nucleotide in the stem region. Adaptor sequences area shown in Table 1.

TABLE 1

| Adaptor sequences | |
|---|---|
| SEQ ID NO: 1 | /5Phos/ATATCTCTCTACTGACTGTCCTCCTCCTCCGTTTTT GAGAGATATT |
| SEQ ID NO: 2 | /5Phos/ATATCTCTCTACTGACTGTCCTCCTCCTCCGTTTTT GAGAGA/ideoxyU/ATT |
| SEQ ID NO: 3 | /5Phos/ATATCTCTCTTTTCCTCCTCCTCCGTTGTTGTTGTT GAGAGATATT |

TABLE 1-continued

| Adaptor sequences | |
|---|---|
| SEQ ID NO: 4 | /5Phos/ATATCTCTCTTTTCCTCCTCCTCCGTTGTTGTTGTT GAGAGA/ideoxyU/ATT |
| SEQ ID NO: 5 | /5Phos/ATCTCTCTCTACTGACTGTCCTCCTCCTCCGTT*T* T*T |

A fragment of HIV genome (HIV Genewiz wildtype DNA (10⁰ copies) amplicon size 1.1 kb) was used as target nucleic acid. 2 ug of the purified PCR product was ligated to the adaptors using commercial library prep reagents (Kapa Biosystems, Wilmington, Mass.). After ligating, the reaction mixture was treated with exonuclease to remove any remaining linear molecules. For the linear adaptor (SEQ ID NO: 5), exonuclease was not used. Qubit was used to determine ssDNA and dsDNA final library concentrations. In the next step, adapted target nucleic acids were digested with a mixture of Uracil DNA glycosylase (UDG) and the DNA glycosylase-lyase Endonuclease VIII (USER™, New England Biolabs, Waltham, Mass.) For adaptors with no uracil (SEQ ID Nos: 1, 3, and 5). USER™ was not used. After the USER™ treatment, a sequencing primer was added. The sequencing primer binding site is in the loop region (FIG. 4). The resulting libraries were sequenced on Pacific BioSciences RSII platform (Pacific Biosciences, Menlo Park, Cal.) and on a nanopore platform (Roche Sequencing Solutions. Santa Clara, Cal.). The quality and length of the sequencing reads on the RSII platform is summarized in Table 2.

TABLE 2

| | Sequencing on RSII platform | | | |
|---|---|---|---|---|
| Adaptor | Cleavage | Polymerase read length (bases) | Read of interest length (bases) | # High quality reads |
| SEQ ID NO: 3 | N/A | 19,156 | 1,047 | 50,836 |
| SEQ ID NO: 4 | USER | 1,208 | 1,208 | 49,104 |
| SEQ ID NO: 4 | none | 18,396 | 1,221 | 5,792 |

Figure 6:
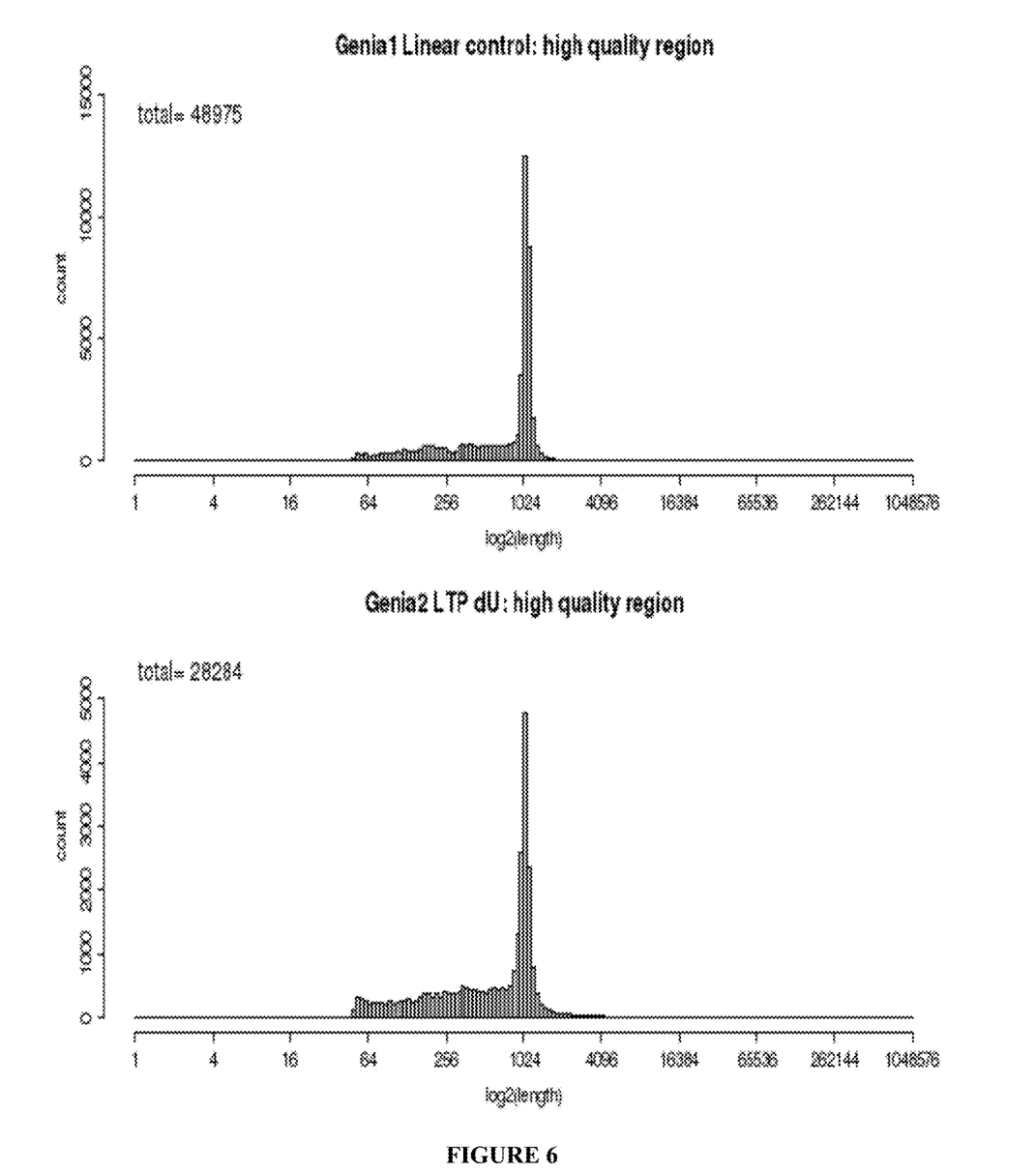
FIG. 6 shows results of sequencing the library on a nanopore sequencer.

The quality and length of the sequencing reads on the nanopore platform is shown in FIG. 6.

Example 2 (Prophetic). Forming and Sequencing a Library with a Self-Priming dU-Containing Hairpin Adaptor In this example, a hairpin adaptor diagrammed in FIG. 7 is used. Adaptor is SEQ ID NO 6:

SEQ ID NO: 6:
/5phos/ATCTCTCTCAAATCCTCCTCCTCCGTTGGAGGAACGGAGGAGG

A*G*G*AUUUGAGAGAGATT

U-deoxyuracils; *- phosphorothioate nucleotides.

The adaptor is ligated to the target nucleic acids using standard library prep reagents (e.g., Kapa Biosystems). The reaction mixture containing adapted target nucleic acids is treated with exonucleases Exo VII and Exo III to enrich for adapted target nucleic acids. The enriched adapted target nucleic acids are treated with UDG and endonuclease Endo IV. UDG cleaves the U and leaves an abasic site, and EndoIV cleaves the abasic site and leaves an open 3'-OH. This step converts the hairpin adapter into a self priming adapter. The adapted nucleic acids with the self-priming adaptor are applied directly to linear sequencing on long-read platforms, such as nanopore platforms. The sequencing polymerase binds to the 3'-OH in the self-priming adaptor and extends the strand by displacing the strand ahead in a linear single-pass sequencing.

Example 3 (Prophetic). Forming and Sequencing a Library with a Self-Priming Ribonucleotide-Containing Hairpin Adaptor In this example, a hairpin adaptor diagrammed in FIG. 7 is used. Adaptor is SEQ ID NO: 7:

```
SEQ ID NO: 7:
/5phos/ATCTCTCTCTTTTCCTCCTCCTCCGTTGGAGGAACGGAGGAGG

A*G*G*ArArArArAGAGAGAGATT rA-ribonucleotides; *-phosphorothioate nucleotides
```

The adaptor is ligated to the target nucleic acids using standard library prep reagents (e.g., Kapa Biosystems). The reaction mixture containing adapted target nucleic acids is treated with exonucleases Exo VII and Exo III to enrich for adapted target nucleic acids. The enriched adapted target nucleic acids are treated with RNaseH, e.g., RNaseH2 that cleaves the ribonucleotide and leaves an open 3'-OH. This step converts the hairpin adaptor into a self-priming adaptor. The adapted nucleic acids with the self-priming adaptor are applied directly to linear sequencing on long-read platforms as in Example 2.

While the invention has been described in detail with reference to specific examples, it will be apparent to one skilled in the art that various modifications can be made within the scope of this invention. Thus the scope of the invention should not be limited by the examples described herein, but by the claims presented below.

The invention claimed is:

1. A method of separately sequencing each strand of a target nucleic acid comprising the steps of:
   a) in a reaction mixture, joining the ends of a double stranded target nucleic acid to adaptors to form a doubly-adapted target nucleic acid wherein the adaptor is a single strand forming a double stranded stem and a single-stranded loop and the stem comprises at least one strand cleavage site;
   b) contacting the reaction mixture with an exonuclease thereby enriching for the doubly-adapted target nucleic acid;
   c) contacting the reaction mixture with a cleavage agent to cleave the doubly-adapted target nucleic acid at the cleavage sites forming extendable termini on each strand;
   d) extending the extendable termini thereby separately sequencing each strand of the target nucleic acid, wherein extension is terminated at the cleavage site and does not proceed onto the complementary strand.

2. The method of claim 1, wherein joining to the adaptor is by ligation.

3. The method of claim 1, wherein the adaptor comprises at least one barcode.

4. The method of claim 1, wherein the cleavage site comprises one or more deoxyuracils and the cleavage agent comprises Uracil-DNA-N-glycosylase (UNG) and an endonuclease.

5. The method of claim 1, wherein the adaptor comprises an exonuclease protection nucleotide.

6. The method of claim 1, wherein the adaptor comprises a ligand for a capture moiety.

7. The method of claim 1, further comprising a target enrichment step prior to sequencing.

8. The method of claim 7 wherein the enrichment is by capture via target-specific probes.

9. A method of determining the sequence of a library of a target nucleic acids for separately sequencing each strand of a target nucleic acid, the method comprising the steps of:
   a) in a reaction mixture, joining the ends of double stranded target nucleic acids to adaptors to form a doubly-adapted target nucleic acids wherein the adaptor is a single strand forming a double stranded stem and a single-stranded loop and the stem comprises a strand cleavage site;
b) contacting the reaction mixture with an exonuclease thereby enriching for the doubly-adapted target nucleic acids;
c) contacting the reaction mixture with a cleavage agent to cleave the doubly-adapted target nucleic acids at the cleavage sites forming extendable termini on each strand;
d) extending the extendable termini thereby separately sequencing each strand of the target nucleic acids in the library, wherein the extension is terminated at the cleavage site and does not proceed onto the complementary strand.

10. A method of separately sequencing each strand of a target nucleic acid comprising the steps of:
a) in a reaction mixture, joining the ends of a double stranded target nucleic acid to adaptors to form a doubly-adapted target nucleic acid wherein the adaptor is a single strand forming a double stranded stem and a single-stranded loop, and the loop comprises a primer binding site and the adaptor further comprises strand synthesis termination site selected from an abasic nucleotide and a non-nucleotide linker and;
b) contacting the reaction mixture with an exonuclease thereby enriching for the doubly-adapted target nucleic acid;
c) contacting the reaction mixture with a primer capable of hybridizing to the primer binding sites;
d) extending the primers thereby separately sequencing each strand of the target nucleic acid, wherein extension is terminated at the strand synthesis termination site and does not proceed onto the complementary strand.

11. A method of determining the sequence of a library for separately sequencing each strand of a target nucleic acid comprising the steps of:
a) in a reaction mixture, joining the ends of double stranded target nucleic acids to adaptors to form doubly-adapted target nucleic acids wherein the adaptor is a single strand forming a double stranded stem and a single-stranded loop, and the loop comprises a primer binding site and the adaptor further comprises strand synthesis termination site;
b) contacting the reaction mixture with an exonuclease thereby enriching for the doubly-adapted target nucleic acids and forming a library of doubly-adapted target nucleic acids;
c) contacting the library with a primer capable of hybridizing to the primer binding sites;
d) extending the primers thereby separately sequencing each strand of the target nucleic acids in the library, wherein extension is terminated at the strand synthesis termination site and does not proceed onto the complementary strand.

12. The method of claim 1, wherein the cleavage site is an abasic site and the cleavage agent is AP nuclease.

13. The method of claim 1, wherein the cleavage site is an 8-oxoguanine and the cleavage agent is 8-oxoguanine DNA glycosylase.

14. The method of claim 1, wherein the cleavage site is a deoxyinosine and the cleavage agent is a combination of alkyladenine glycosylase (AAG) and endonuclease.

15. The method of claim 1, wherein the cleavage site is a ribonucleotide and the cleavage agent is RNaseH.

* * * * *

SEQUENCE LISTING

```
<160> NUMBER OF SEQ ID NOS: 7

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded artificial

<400> SEQUENCE: 1
atatctctct actgactgtc ctcctcctcc gtttttgaga gatatt                46

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded artificial

<400> SEQUENCE: 2
atatctctct actgactgtc ctcctcctcc gtttttgaga gatatt                46

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded artificial

<400> SEQUENCE: 3
atatctctct tttcctcctc ctccgttgtt gttgttgaga gatatt                46

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Single stranded artificial

<400> SEQUENCE: 4
atatctctct tttcctcctc ctccgttgtt gttgttgaga gatatt            46

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded artificial

<400> SEQUENCE: 5
atctctctct actgactgtc ctcctcctcc gttttt                       36

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded artificial

<400> SEQUENCE: 6
atctctctca aatcctcctc ctccgttgga ggaacggagg aggaggattt gagagagatt    60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded artificial

<400> SEQUENCE: 7
atctctctct tttcctcctc ctccgttgga ggaacggagg aggaggaaaa gagagagatt    60
```